(12) United States Patent
Mitsumatsu

(10) Patent No.: US 6,368,582 B1
(45) Date of Patent: Apr. 9, 2002

(54) HAIR CONDITIONING COMPOSITIONS COMPRISING WATER-INSOLUBLE HIGH MOLECULAR WEIGHT OILY COMPOUND

(75) Inventor: Arata Mitsumatsu, Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/319,470

(22) PCT Filed: Dec. 6, 1996

(86) PCT No.: PCT/US96/19397

§ 371 Date: Jun. 4, 1999

§ 102(e) Date: Jun. 4, 1999

(87) PCT Pub. No.: WO98/24401

PCT Pub. Date: Jun. 11, 1998

(51) Int. Cl.$^7$ ............................. A61K 7/06; A61K 7/00
(52) U.S. Cl. ............... 424/70.11; 424/70.1; 424/70.12; 424/70.13; 424/70.27; 424/70.28
(58) Field of Search ............................ 424/70.1, 70.11, 424/70.12, 70.13, 70.27, 70.28

(56) References Cited

U.S. PATENT DOCUMENTS 4,175,572 A * 11/1979 Hsiung et al.

OTHER PUBLICATIONS

Harry's Cosmeticology (7th Ed., Chemical Publishing, New York, 1982) p. 493.*

* cited by examiner

Primary Examiner—Thurman K. Page
Assistant Examiner—Brian K. Seidleck
(74) Attorney, Agent, or Firm—Linda M. Sivik; Tara M. Rosnell; Brahm J. Corstanje

(57) ABSTRACT

Disclosed are hair conditioning compositions comprising a water-insoluble high molecular weight oily compound having a molecular weight of at least about 800, specific gravity of at least about 0.9, is in a liquid form at 25° C. and has formula (I):

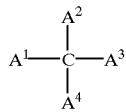

wherein $A^1$, $A^2$, $A^3$ and $A^4$ are independently alkyl, alkenyl, aryl, alkylaryl, hydroxyalkyl, alkoxyl, alkoxyalkyl, acyl, acylalkyl, and alkylacyloxyl group having $C_1$ to about $C_{30}$ or the formula —$(CH_2)_n$—O—OCR wherein R is from $C_1$ to about $C_{30}$ of branched or straight chain alkyl or alkenyl and n is an integer from 1 to about 30; and a carrier.

18 Claims, No Drawings

HAIR CONDITIONING COMPOSITIONS COMPRISING WATER-INSOLUBLE HIGH MOLECULAR WEIGHT OILY COMPOUND

This application is a 371 of PCT/US 96/19397 filed Dec. 6, 1996.

TECHNICAL FIELD

The present invention relates to hair conditioning compositions comprising a water-insoluble high molecular weight oily compound.

BACKGROUND

Human hair becomes soiled due to its contact with the surrounding environment and from sebum secreted by the scalp. The soiling of the hair causes it to have a dirty or greasy feel, and an unattractive appearance. The soiling of the hair necessitates shampooing with regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying which can interfere with combing and result in a condition commonly referred to as "fly-away hair", or contribute to an undesirable phenomena of "split ends", particularly for long hair.

A variety of approaches have been developed to alleviate these after-shampoo problems. These approaches range from post-shampoo application of hair conditioner such as leave-on and rinse-off products, to hair conditioning shampoos which attempt to both cleanse and condition the hair from a single product. Although some consumers prefer the ease and convenience of a shampoo which includes conditioners, a substantial proportion of consumers prefer the more conventional conditioner formulations which are applied to the hair as a separate step from shampooing, usually subsequent to shampooing. Conditioning formulation can be in the form of rinse-off products or leave-on products, and can be in the form of an emulsion, cream, gel, spray, and mousse. Such consumers who prefer the conventional conditioner formulations value the relatively higher conditioning effect, or convenience of changing the amount of conditioning depending on the condition of hair or portion of hair. Further, consumers prefer conditioners which provide smoothness and softness to the hair and wet combing benefits.

A common method of providing conditioning benefit to the hair is through the use of hair conditioning agents such cationic surfactants and polymers, silicone conditioning agents, and hydrocarbon and other organic oils, and solid aliphatics such as fatty alcohols. Cationic surfactants and polymers, as well as oils and aliphatics are known to enhance hair shine and provide moistness, softness, and static control to the hair, however, are also known to provide stickiness or greasy or waxy feeling.

High molecular weight substances, for example, silicone polymers are also known to provide conditioning benefits such as smoothness and combing ease. Without being bound by theory, it is believed that, due to the low surface tension of silicone polymers, silicone polymer provides favorable conditioning benefits to the hair. However, a large amount of silicone polymer compound causes dry feel or frizzy condition.

Japan Laid open S55-124711 discloses a hair composition comprising a branched ester such as pentaerythritol monoisostearate, methylphenyl-silicone compound, polyoxyethylene fatty acid ester and water. Japan Laid open H5-124921 discloses a cosmetic composition comprising a nonionic amphiphilic compound having at least one long chain branched alkyl or alkenyl group and structure of a lamellar liquid crystal. The nonionic amphiphilic includes methyl branched fatty acid ester of pentaerythritol.

There remains a desire to provide hair conditioning compositions with improved conditioning benefits such as smoothness, softness, and ease of combing when the hair is wet.

In the present invention, a hair conditioning composition comprising a water-insoluble high molecular weight oily compound which is in a liquid form and has a molecular weight of at least about 800 has been developed. This hair conditioning composition provides improved conditioning benefits such as moistness, softness, free flowing, decreased stickiness, and static control, and which known conditioning agents can be incorporated in the composition.

SUMMARY

The present invention relates to a hair conditioning composition comprising:

(a) a water-insoluble high molecular weight oily compound having a molecular weight of at least about 800, specific gravity of at least about 0.9, is in a liquid form at 25° C., and has the following formula (I):

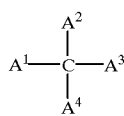

(I)

wherein $A^1$, $A^2$, $A^3$ and $A^4$ are independently alkyl, alkenyl, aryl, alkylaryl, hydroxyalkyl, alkoxyl, alkoxyalkyl, acyl, acylalkyl, and alkylacyloxyl group having $C_1$ to about $C_{30}$ or the formula $-(CH_2)_n-O-OCR$ wherein R is from $C_1$ to about $C_{30}$ of branched or straight chain alkyl or alkenyl and n is an integer from 1 to about 30; and (b) a carrier.

Such compositions satisfy the need for a hair conditioning composition which has improved conditioning benefits such as moistness, softness, free flowing, decreased stickiness, and static control, and which known conditioning agents can be incorporated in the composition.

DETAILED DESCRIPTION

All percentages herein are by weight of the compositions unless otherwise indicated. All ratios are weight ratios unless otherwise indicated. All percentages, ratios, and levels of ingredients referred to herein are by weight and are based on the actual amount of the ingredient, and do not include solvents, fillers, or other materials with which the ingredient may be combined as commercially available products, unless otherwise indicated.

The invention hereof can comprise, consist of, or consist essentially of the essential elements described herein as well as any of the preferred or optional ingredients also described herein.

All publications, patent applications, and issued patents mentioned herein are hereby incorporated in their entirety by reference.

Water-Insoluble High Molecular Weight Oily Compound

The hair conditioning composition of the present invention comprises a water-insoluble high molecular weight oily compound and a carrier. The water-insoluble high molecular weight oily compounds of the present invention are those which provide excellent conditioning benefits such as smoothness to the hair and ease of combing. Without being bound by theory, it is believed that, the water-insoluble high molecular weight oily compound of this invention is capable of being deposited on and conditions the hair. It is also believed that this water-insoluble high molecular weight oily compound covers the surface of the hair and as a result reduces hair friction to deliver smoothness to the hair. The water-insoluble high molecular weight oily compound is chemically stable under normal use and storage conditions.

As used herein, the term "water-insoluble oily compound" is meant that the compound is not sufficiently soluble in water at room temperature. When the compound is mixed with water at above 1.0% concentration, more preferably at above 0.5% concentration, the compound is temporarily dispersed to form unstable colloid in water, then is quickly separated from water into two phases in a short period.

The water-insoluble high molecular weight oily compound useful in the present invention has a molecular weight of at least about 800, preferably at least about 1000, more preferably at least about 1200 as long as the compound has a specific gravity of at least about 0.9, and is in a liquid form at 25° C.

The water-insoluble high molecular weight oily compound useful herein include those of the following formula (I):

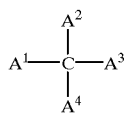

wherein $A^1$, $A^2$, $A^3$ and $A^4$ are independently alkyl, alkenyl, aryl, alkylaryl, hydroxyalkyl, alkoxyl, alkoxyalkyl, acyl, acylalkyl, and alkylacyloxyl group having $C_1$ to about $C_{30}$ or the formula —$(CH_2)_n$—O—OCR wherein R is from $C_1$ to about $C_{30}$ of branched or straight chain alkyl or alkenyl and n is an integer from 1 to about 30, and preferably equals 1.

Preferably, the water-insoluble high molecular weight oily compound of this invention is an ester wherein all of $A^1$, $A^2$, $A^3$ and $A^4$ are ester groups or three of $A^1$, $A^2$, $A^3$ and $A^4$ are ester groups and the remainder is an alkyl group. More preferably, the water-insoluble high molecular weight oily compounds of this invention are esters of a fatty acid of from about $C_{12}$ to about $C_{22}$ with pentaerythritol, esters of a fatty acid of from about $C_{12}$ to about $C_{22}$ with trimethylolalkane, and mixtures thereof.

Preferable water-insoluble high molecular weight oily compounds are those which have the same substituent for $A^1$, $A^2$, $A^3$ and $A^4$ and wherein these substituents are ester groups.

The preferred water-insoluble high molecular weight oily compounds of this invention are pentaerythritol tetraisostearate, trimethylolpropane triisostearate, pentaerythritol tetraoleate, trimethylolpropane trioleate, and mixtures thereof.

Suitable ester compounds include, for example, pentaerythritol tetraisostearate and trimethylolpropane triisostearate which are available from Kokyo Alcohol with tradenames KAKPTI and KAKTTI, and pentaerythritol tetraoleate and trimethylolpropane trioleate which are available from Shinnihon Rika with tradenames PTO and ENUJERUBU TP3SO, respectively.

The water-insoluble high molecular weight oily compound is used at a level of from about 0.1% to about 20.0%, preferably from about 0.1% to about 10.0%, more preferably from about 0.2% to about 5.0% by weight of the composition.

Carrier

The hair conditioning composition of the present invention comprises a carrier. The level and species of the carrier are selected according to the compatibility with other components, and desired characteristic of the product.

The carrier useful in the present invention include water, lower alkyl alcohols, polyhydric alcohols, and mixtures thereof. The lower alkyl alcohol useful herein are $C_1$–$C_6$ alkyl monohydric alcohols, preferably $C_2$–$C_3$ alkyl alcohols. The preferred lower alkyl alcohol is ethyl alcohol, isopropyl alcohol, and mixtures thereof. The polyhydric alcohols useful herein include, for example, propylene glycol, hexylene glycol, glycerin, and propane diol, and mixture thereof.

Nonvolatile Water-Insoluble Low Molecular Weight Oily Compound

The hair conditioning composition of the present invention may further comprise a nonvolatile water-insoluble low molecular weight oily compound. The nonvolatile water-insoluble low molecular weight oily compounds of the present invention are those which provide excellent conditioning benefits to the hair. Without being bound by theory, it is believed that, the nonvolatile water-insoluble low molecular weight oily compounds may penetrate to the hair easily and result in providing softness to the hair and increasing hair flexibility.

As used herein, the term "nonvolatile" is meant that the water-insoluble low molecular weight oily compounds exhibit very low or no significant vapor pressure at ambient conditions, e.g., 1 atmosphere at 25° C.

The nonvolatile water-insoluble low molecular weight oily compound useful in the present invention has a molecular weight of less than about 800, preferably less than about 500, and more preferably less than about 300 as long as the compound has a specific gravity of at least about 0.8 and is in a liquid form at 25° C.

Preferably, the nonvolatile water-insoluble low molecular weight oily compound useful herein is selected from the group consisting of hydrocarbon having from 10 to about 40 carbon atoms, fatty alcohols having from about 10 to about 30 carbon atoms, fatty acids having from about 10 to about 30 carbon atoms, fatty acid derivatives, fatty alcohol derivatives, and mixtures thereof.

Useful hydrocarbons include straight chain, cyclic, and branched chain hydrocarbons which can be either saturated or unsaturated. Suitable hydrocarbons having from 10 to about 40 carbon atoms include, for example isoparaffin and mineral oil. These hydrocarbons are available, for example, from Exxon Chemical Co. with tradenames Isopar and Witco Corp. with tradenames Benol.

The fatty alcohols useful herein include those having from about 10 to about 30 carbon atoms, preferably from about 12 to about 22 carbon atoms, and more preferably from about 16 to about 22 carbon atoms. These fatty alcohols can be straight or branched chain alcohols and can be saturated or unsaturated alcohols, preferably unsaturated alcohols. Suitable fatty alcohols include, for example, oleyl alcohol, isostearyl alcohol, tridecylcohol, decyl tetradecyl alcohol, and octyl dodecyl alcohol. These alcohols are available, for example, from Shinnihon Rika.

The fatty acids useful herein include those having from about 10 to about 30 carbon atoms, preferably from about 12 to about 22 carbon atoms, and more preferably from about 16 to about 22 carbon atoms. These fatty acids can be straight or branched chain acids and can be saturated or unsaturated. Suitable fatty acids include, for example, oleic acid, linoleic acid, isostearic acid, linolenic acid, and ethyl linolenic acid.

The fatty acid derivatives and fatty alcohol derivatives are defined herein to include, for example, esters of fatty alcohols, alkoxylated fatty alcohols, alkyl ethers of fatty alcohols, alkyl ethers of alkoxylated fatty alcohols, and mixtures thereof. Nonlimiting examples of fatty acid derivatives and fatty alcohol derivatives, include, for example, methyl linoleate, ethyl linoleate, isopropyl linoleate, isodecyl oleate, isopropyl oleate, ethyl oleate, octyidodecyl oleate, oleyl oleate, decyl oleate, butyl oleate, methyl oleate, octyldodecyl stearate, octyldodecyl isostearate, octyiodecyl isopalmitate, octyl isopelargonate, octyl pelargonate, hexyl isostearate, isopropyl isostearate, isodecyl isononanoate, and Oleth-2.

Highly preferred nonvolatile water-insoluble low molecular weight oily compound is selected from the group consisting of octyl dodecyl isostearate, methyl myristate, oleyl alcohol, hydrocarbons having from about 14 to about 40 of carbon atoms, and mixtures thereof.

Nonlimiting examples of the above compounds are found in International Cosmetic Ingredient Dictionary, Fifth Edition, 1993, and CTFA Cosmetic Ingredient Handbook, Second Edition, 1992, both of which are incorporated by reference herein in their entirety.

The nonvolatile low molecular weight oily compound is comprised at a level of from about 0.1% to about 10.0%, preferably from about 0.2% to about 5.0%, more preferably from about 0.2% to about 2.0% by weight of the composition.

Solid Water-Insoluble Aliphatic Compound

The hair conditioning composition of the present invention may further comprise a solid water-insoluble aliphatic compound. Without being bound by theory, it is believed that, the solid water-insoluble aliphatic compound of this invention covers the hair surface, and provides smooth feel on the hair and ease of combing by reducing friction coefficient.

As used herein, the term "solid water-insoluble" aliphatic compound is meant that the compound is not sufficiently soluble in water at room temperature. When the compound is mixed with water at above 1.0% concentration, more preferably at above 0.5% concentration, the compound remains in the original state and does not dissolve. By the term "solid" what is meant is that the compound has a resistance to pressure, does not easily change in shape, and is distinguished from a gum, paste, liquid or gaseous property at 25° C.

The solid water-insoluble aliphatic compound useful in the present invention include those selected from the group consisting of hydrocarbons having at least about 20 carbon atoms, saturated fatty alcohols having at least about 14 carbon atoms, fatty acids having at least about 10 carbon atoms, fatty acid derivatives, fatty alcohol derivatives, steroids, and mixtures thereof. The solid water-insoluble aliphatic compounds such as hydrocarbons, saturated fatty alcohols, fatty acids, fatty acid derivatives or fatty alcohol derivatives are distinguished from the compounds exemplified in the part of "nonvolatile water-insoluble low molecular weight oily compound" in view of its different characteristics.

It is recognized that some of these compounds can have properties as nonionic surfactants and can alternatively be classified as such. However, a given classification is not intended to be a limitation on that particular compound, but is done so for convenience of classification and nomenclature.

The saturated fatty alcohols useful herein are those having at least about 14 carbon atoms, preferably from about 14 to about 22 carbon atoms. These saturated fatty alcohols can be straight or branched chain alcohols. Suitable saturated fatty alcohols include, for example, cetyl alcohol, stearyl alcohol, and behenyl alcohol. These are commercially available, for example, from Shinnihon Rika with tradenames Konol series, or from Nippon Oil with tradenames NAA series.

The fatty acids useful herein are those having at least about 10 carbon atoms. These fatty acids can be straight or branched chain acids and can be saturated or unsaturated. Also included are diacids, triacids, and other multiple acids which meet the carbon number requirement herein. Suitable fatty acids include, for example, stearic acid, behenic acid, palmitic acid, archidonic acid and sebacic Acid. These are available, for example, from Akzo with tradenames Noe-Fat, from Witco Corp. with tradenames Hystrene, or from Vevy with tradenames derma.

The fatty acid derivatives and the fatty alcohol derivatives are defined wherein to include ester of the fatty acids, including the fatty alcohol esters of the acid and the ethoxylated alcohol esters of the acid. Nonlimiting examples of fatty acid derivatives and fatty alcohol derivatives include, for example, glyceryl monostearate, stearyl stearate, ethyl stearate, cetyl stearate, cetyl palmitate and myristyl myristate.

Suitable steroids include, for example, cholesterol, from Nikko with tradenames Nikkol Aguasome LA.

A highly preferred solid water-insoluble aliphatic compound is saturated fatty alcohol having from about $C_{14}$ to about $C_{22}$.

Nonlimiting examples of the above compounds are found in International Cosmetic Ingredient Dictionary, Fifth Edition, 1993, and CTFA Cosmetic Ingredient Handbook, Second Edition, 1992, both of which are incorporated by reference herein in their entirety.

The solid water-insoluble aliphatic compound is comprised at the level of from about 0.1% to about 20%, preferably from about 1% to about 15%, more preferably from about 4% to about 10% of the composition.

Additional Conditioning Agents

In addition, other conditioning agents known in the industry may be comprised in the present invention. Suitable conditioning agents include cationic surfactants, cationic polymers, silicone compounds, and mixtures thereof. These conditioning agents are comprised at a level of from about 0.01% to about 20% of the conditioning composition of the present invention.

Cationic Surfactant

The hair conditioning compositions of the present invention can additionally-comprise one or more cationic surfactants as a conditioning agent.

The cationic surfactants useful herein are any known to the artisan.

Among the cationic surfactants useful herein are those corresponding to the general formula (I):

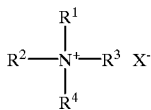
(I)

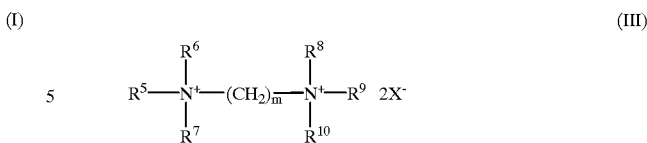
(III)

wherein m is 1 to 5, one or more of $R^5$, $R^6$, and $R^7$ are independently an $C_1$–$C_{30}$ alkyl, the remainder are —$CH_2CH_2OH$, one or two of $R^8$, $R^9$, and $R^{10}$ are independently an $C_1$–$C_{30}$ alkyl, and remainder are —$CH_2CH_2OH$, and X is a salt forming anion as mentioned above;

wherein at least one of $R^1$, $R^2$, $R^3$, and $R^4$ is selected from an aliphatic group of from 8 to 30 to carbon atoms or an aromatic, alkoxy, polyoxyalkylene, alkylamido, hydroxyalkyl, aryl or alkylaryl group having up to about 22 carbon atoms, the remainder of $R^1$, $R^2$, $R^3$, and $R^4$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^1$, $R^2$, $R^3$, and $R^4$ are independently selected from $C_1$ to about $C_{22}$ alkyl. Nonlimiting examples of cationic surfactants useful in the present invention include the materials having the following CTFA designations: quaternium-8, quaternium-24, quaternium-26, quaternium-27, quaternium-30, quaternium-33, quaternium-43, quaternium-52, quaternium-53, quaternium-56, quaternium-60, quaternium-62, quaternium-70, quaternium-72, quaternium-75, quaternium-77, quaternium-78, quaternium-80, quaternium-81, quaternium-82, quaternium-83, quaternium-84, and mixtures thereof.

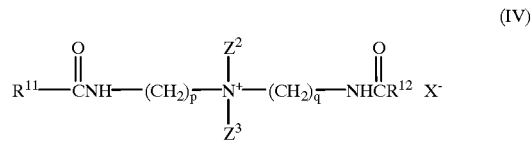
(IV)

wherein $Z^2$ is an alkyl, preferably a $C_1$–$C_3$ alkyl, more preferably methyl, and $Z^3$ is a short chain hydroxyalkyl, preferably hydroxymethyl or hydroxyethyl, p and q independently are integers from 2 to 4, inclusive, preferably from 2 to 3, inclusive, more preferably 2, $R^{11}$ and $R^{12}$, independently, are substituted or unsubstituted hydrocarbyls, preferably $C_{12}$–$C_{20}$ alkyl or alkenyl, and X is a salt forming anion as defined above;

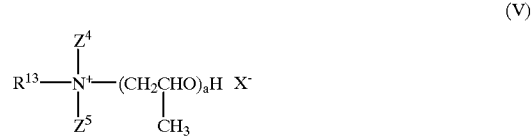
(V)

wherein $R^{13}$ is a hydrocarbyl, preferably a C1–C3 alkyl, more preferably methyl, $Z^4$ and $Z^5$ are, independently, short chain hydrocarbyls, preferably C2–C4 alkyl or alkenyl, more preferably ethyl, a is from 2 to about 40, preferably from about 7 to about 30, and X is a salt forming anion as defined above;

Also preferred are hydrophilically substituted cationic surfactants in which at least one of the substituents contain one or more aromatic, ether, ester, amido, or amino moieties present as substituents or as linkages in the radical chain, wherein at least one of the $R^1$–$R^4$ radicals contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof. Preferably, the hydrophilically substituted cationic conditioning surfactant contains from 2 to about 10 nonionic hydrophile moieties located within the above stated ranges. Preferred hydrophilically substituted cationic surfactants include those of the formula (II) through (VII) below:

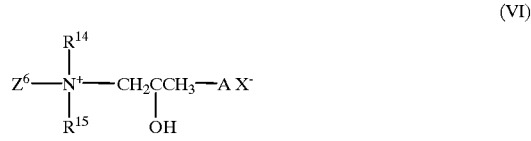
(VI)

wherein $R^{14}$ and $R^{15}$, independently, are $C_1$–$C_3$ alkyl, preferably methyl, $Z^6$ is a $C_{12}$–$C_{22}$ hydrocarbyl, alkyl carboxy or alkylamido, and A is a protein, preferably a collagen, keratin, milk protein, silk, soy protein, wheat protein, or hydrolyzed forms thereof; and X is a salt forming anion as defined above;

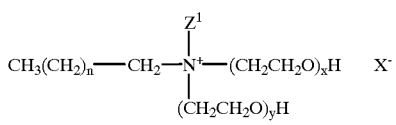
(II)

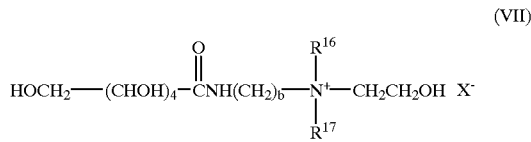
(VII)

wherein n is from 8 to about 28, x+y is from 2 to about 40, $Z^1$ is a short chain alkyl, preferably a $C_1$–$C_3$ alkyl, more preferably methyl, or—$(CH_2CH_2O)_zH$ wherein x+y+z is up to 60, and X is a salt forming anion as defined above;

wherein b is 2 or 3, $R^{16}$ and $R^{17}$, independently are $C_1$–$C_3$ hydrocarbyls preferably methyl, and X is a salt forming anion as defined above. Nonlimiting examples of hydrophilically substituted cationic surfactants useful in the present invention include the materials having the following CTFA designations: quaternium-16, quaternium-61, quaternium-71, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein. Highly preferred compounds include commercially available materials; VARIQUAT K1215 and 638 from Witco Chemical, MACKPRO KLP, MACKPRO WLW, MACKPRO MLP, MACKPRO NSP, MACKPRO NLW, MACKPRO WWP, MACKPRO NLP, MACKPRO SLP from McIntyre, ETHOQUAD 18/25, ETHOQUAD O/12PG, ETHOQUAD C/25, ETHOQUAD S/25, and ETHODUOQUAD from Akzo, DEHYQUAT SP from Henkel, and ATLAS G265 from ICI Americas.

Salts of primary, secondary, and tertiary fatty amines are also suitable cationic surfactants. The alkyl groups of such amines preferably have from about 12 to about 22 carbon atoms, and can be substituted or unsubstituted. Particularly useful are amido substituted tertiary fatty amines. Such amines, useful herein, include stearamidopropyidimethylamine, stearamidopropyldiethylamine, stearamidoethyidiethylamine, stearamidoethyidimethylamine, palmitamidopropyidimethylamine, palmitamidopropyldiethylamine, palmitamidoethyldiethylamine, palmitamidoethyldimethylamine, behenamidopropyldimethylamine, behenamidopropyidiethylamine, behenamidoethyldiethylamine, behenamidoethyidimethylamine, arachidamidopropyldimethylamine, arachidamidopropyidiethylamine, arachidamidoethyldiethylamine, arachidamidoethyidimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidylbehenylamine. These amines can also be used in combination with acids such as L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid. Cationic amine surfactants included among those useful in the present invention are disclosed in U.S. Pat. No. 4,275,055, Nachtigal, et al., issued Jun. 23, 1981, which is incorporated by reference herein in its entirety.

The cationic surfactants for use herein may also include a plurality of ammonium quaternary moieties or amino moieties, or a mixture thereof.

The cationic surfactants for use herein may be used as emulsifying agents in this composition.

Cationic Polymers

The hair conditioning compositions of the present invention can further comprise one or more cationic polymer as a conditioning agent. As used herein, the term "polymer" shall include materials whether made by polymerization of one type of monomer or made by two (i.e., copolymers) or more types of monomers.

Preferably, the cationic polymer is a water-soluble cationic polymer. By "water soluble" cationic polymer, what is meant is a polymer which is sufficiently soluble in water to form a substantially clear solution to the naked eye at a concentration of 0.1% in water (distilled or equivalent) at 25° C. The preferred polymer will be sufficiently soluble to form a substantially clear solution at 0.5% concentration, more preferably at 1.0% concentration.

The caffonic polymers hereof will generally have a weight average molecular weight which is at least about 5,000, typically at least about 10,000, and is less than about million. Preferably, the molecular weight is from about 100,000 to about 2 million. The cationic polymers will generally have cationic nitrogen-containing moieties such as quaternary ammonium or cationic amino moieties, and mixtures thereof.

The cationic charge density is preferably at least about 0.1 meq/gram, more preferably at least about 1.5 meq/gram, even more preferably at least about 1.1 meq/gram, still more preferably at least about 1.2 meq/gram. Cationic charge density of the cationic polymer can be determined according to the Kjeldahl Method. Those skilled in the art will recognize that the charge density of amino-containing polymers may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyidiallylammonium chloride homopolymer and copolymers of acrylamide and dimethyidiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

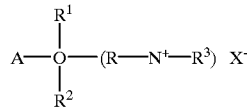

wherein: A is an anhydroglucose residual group, such as a starch or cellulose anhydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200®.

Other cationic polymers that can be used include cationic guar gum derivatives, such as guar hydroxypropyltrimonium chloride (commercially available from Celanese Corp. in their Jaguar R series). Other materials include quaternary nitrogen-containing cellulose ethers (e.g., as described in U.S. Pat. No. 3,962,418, incorporated herein by reference), and copolymers of etherified cellulose and starch (e.g., as described in U.S. Pat. No. 3,958,581, incorporated herein by reference.)

Silicone Compounds

Other conditioning agents useful herein include silicone compounds. The hair conditioning compositions hereof can include volatile soluble or insoluble, or nonvolatile soluble or insoluble silicone conditioning agents. By soluble what is meant is that the silicone conditioning agent is miscible with the carrier of the composition so as to form part of the same phase. By insoluble what is meant is that the silicone forms a separate, discontinuous phase from the carrier, such as in the form of an emulsion or a suspension of droplets of the silicone.

The nonvolatile dispersed silicones for use herein will preferably have a viscosity of from about 1,000 to about 2,000,000 centistokes at 25° C., more preferably from about 10,000 to about 1,800,000, and even more preferably from about 100,000 to about 1,500,000. The viscosity can be measured by means of a glass capillary viscometer as set forth in Dow Corning Corporate Test Method CTM0004, Jul. 20, 1970, which is incorporated by reference herein in its entirety. Suitable silicone fluids include polyalkyl siloxanes, polyaryl siloxanes, polyalkylaryl siloxanes, polyether siloxane copolymers, and mixtures thereof. Other nonvolatile silicone compounds having hair conditioning properties can also be used.

The nonvolatile dispersed silicone compounds herein also include polyalkyl or polyaryl siloxanes with the following structure (I)

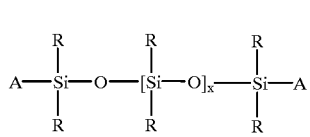

wherein R is alkyl or aryl, and x is an integer from about 7 to about 8,000. "A" represents groups which block the ends of the silicone chains. The alkyl or aryl groups substituted on the siloxane chain (R) or at the ends of the siloxane chains (A) can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable A groups include hydroxy, methyl, methoxy, ethoxy, propoxy, and aryloxy. The two R groups on the silicon atom may represent the same group or different groups. Preferably, the two R groups represent the same group. Suitable R groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their ViscasilR and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicone compounds, such as highly phenylated polyethyl silicone having refractive index of about 1.46 or higher, especially about 1.52 or higher. When these high refractive index silicone compounds are used, they should be mixed with a spreading agent, such as a surfactant or a silicone resin, as described below to decrease the surface tension and enhance the film forming ability of the material.

The nonvolatile dispersed silicone compounds that can be used include, for example, a polypropylene oxide modified polydimethylsiloxane although ethylene oxide or mixtures of ethylene oxide and propylene oxide can also be used. The ethylene oxide and polypropylene oxide level should be sufficiently low so as not to interfere with the dispersibility characteristics of the silicone. These material are also known as dimethicone copolyols.

Other nonvolatile dispersed silicone compounds include amino substituted materials. Suitable alkylamino substituted silicone compounds include those represented by the following structure (II)

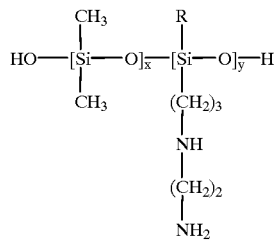

wherein R is $CH_3$ or OH, x and y are integers which depend on the molecular weight, the average molecular weight being approximately between 5,000 and 10,000. This polymer is also known as "amodimethicone".

Suitable amino substituted silicone fluids include those represented by the formula (III)

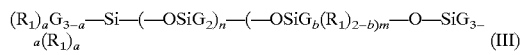

in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical of formula $CqH_{2q}L$ in which q is an integer from 2 to 8 and L is chosen from the groups

—$N(R_2)CH_2$—$CH_2$—$N(R_2)_2$

—$N(R_2)_2$

—$N(R_2)_3A^-$

—$N(R_2)CH_2$—$CH_2$—$NR_2H_2A^-$ in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

An especially preferred amino substituted silicone corresponding to formula (III) is the polymer known as "trimethylsilylamodimethicone", of formula (IV):

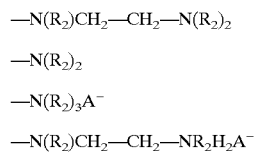

(IV)

In this formula n and m are selected depending on the exact molecular weight of the compound desired.

Other amino substituted silicone polymers which can be used are represented by the formula (V):

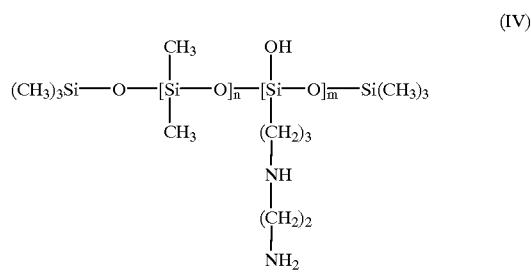

(V)

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

References disclosing suitable nonvolatile dispersed silicone compounds include U.S. Pat. No. 2,826,551, to Geen; U.S. Pat. No. 3,964,500, to Drakoff, issued Jun. 22, 1976; U.S. Pat. No. 4,364,837, to Pader; and British Patent No. 849,433, to Woolston, all of which are incorporated herein by reference in their entirety. Also incorporated herein by reference in its entirety is "Silicon Compounds" distributed by Petrarch Systems, Inc., 1984. This reference provides an extensive, though not exclusive, listing of suitable silicone compounds.

Another nonvolatile dispersed silicone that can be especially useful is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. Silicone gums are described by Petrarch, and others including U.S. Pat. No. 4,152,416, to Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference in their entirety. The "silicone gums" will typically have a mass molecular weight in excess of about 200,000, generally between about 200,000 and about 1,000,000. Specific examples include polydimethylsiloxane, poly (dimethylsiloxane methylvinylsiloxane) copolymer, poly (dimethylsiloxane diphenylsiloxane methylvinylsiloxane) copolymer and mixtures thereof.

Also useful are silicone resins, which are highly crosslinked polymeric siloxane systems. The crosslinking is introduced through the incorporation of tri-functional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinylchlorosilanes, and tetrachlorosilane, with the methyl substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being bound by theory, it is believed that the silicone resins can enhance deposition of other silicone compounds on the hair and can enhance the glossiness of hair with high refractive index volumes.

Other useful silicone resins are silicone resin powders such as the material given the CTFA designation polymethylsilsequioxane, which is commercially available as Tospearl™ from Toshiba Silicones.

Background material on silicone compounds, including sections discussing silicone fluids, gums, and resins, as well as the manufacture of silicone compounds, can be found in Encyclopedia of Polymer Science and Engineering, Volume 15, Second Edition, pp 204–308, John Wiley & Sons, Inc., 1989, which is incorporated herein by reference in its entirety.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the monofunctional unit $(CH_3)_3SiO_{.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M andor or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTO, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

Additional Surfactants

Hair conditioning compositions of the present invention may further comprise additional surfactants. Such additional surfactants comprise amphoteric surfactants, zwitterionic surfactants, nonionic surfactants, anionic surfactants, and mixtures thereof which do not affect the conditioning composition of the present invention.

The additional surfactant is particularly useful for compositions in the form of spray or mousse, wherein the additional surfactant is used to suspend the conditioning agents and other components which are insoluble in the carrier. Additional surfactants are typically included at a level by weight of from about 0.1% to about 15%, preferably from about 0.3% to about 10% of the composition. The level and species are selected according to the compatibility with other components, and desired characteristic of the product.

Amphoteric and Zwitterionic Surfactants

The hair conditioning compositions of the present invention can comprise amphoteric and or zwifterionic surfactants.

Amphoteric surfactants for use herein include the derivatives of aliphatic secondary and tertiary amines in which the aliphatic radical is straight or branched and one of the aliphatic substituents contains from about 8 to about 18 carbon atoms and one contains an anionic water solubilizing group, e.g., carboxy, sulfonate, sulfate, phosphate, or phosphonate.

Zwitterionic surfactants for use herein include the derivatives of aliphatic quaternary ammonium, phosphonium, and sulfonium compounds, in which the aliphatic radicals are straight or branched, and wherein one of the aliphatic substituents contains from about 8 to about 18 carbon atoms and one contains an anionic group, e.g., carboxy, sulfonate, sulfate, phosphate, or phosphonate. A general formula for these compounds is:

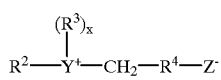

where $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom, and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples of amphoteric and zwitterionic surfactants also include sultaines and amidosultaines. Sultaines, including amidosultaines, include for example, cocodimethylpropylsultaine, stearyldimethylpropylsultaine, lauryl-bis-(2-hydroxyethyl)propylsultaine and the like; and the amidosultaines such as cocamidodimethylpropylsultaine, stearylamidododimethylpropylsultaine, laurylamido-bis-(2-hydroxyethyl)propylsultaine, and the like. Preferred are amidohydroxysultaines such as the $C_{12}$–$C_{18}$ hydrocarbylamidopropylhydroxysultaines, especially $C_{12}$–$C_{14}$ hydrocarbylamidopropylhydroxysultaines, e.g., laurylamidopropylhydroxysultaine and cocamidopropylhydroxysultaine. Other sultaines are described in U.S. Pat. No. 3,950,417, which is incorporated herein by reference in its entirety.

Other suitable amphoteric surfactants are the aminoalkanoates of the formula $RNH(CH_2)_nCOOM$, the iminodialkanoates of the formula $RN[(CH_2)_mCOOM]_2$ and mixtures thereof; wherein n and m are numbers from 1 to about 4, R is $C_8$–$C_{22}$ alkyl or alkenyl, and M is hydrogen, alkali metal, alkaline earth metal, ammonium or alkanolammonium.

Examples of suitable aminoalkanoates include n-alkylaminopropionates and n-alkyliminodipropionates, specific examples of which include N-lauryl-beta-amino propionic acid or salts thereof, and N-lauryl-beta-iminodipropionic acid or salts thereof, and mixtures thereof.

Other suitable amphoteric surfactants include those represented by the formula:

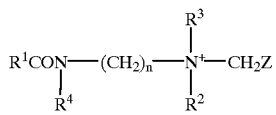

wherein $R^1$ is $C_8$–$C_{22}$ alkyl or alkenyl, preferably $C_{12}$–$C_{16}$, $R^2$ and $R^3$ is independently selected from the group consisting of hydrogen, $—CH_2CO_2M$, $—CH_2CH_2OH$, $—CH_2CH_2OCH_2CH_2COOM$, or $—(CH_2CH_2O)_mH$ wherein m is an integer from 1 to about 25, and $R^4$ is hydrogen, $—CH_2CH_2OH$, or $CH_2CH_2OCH_2CH_2COOM$, Z is $CO_2M$ or $CH_2CO_2M$, n is 2 or 3, preferably 2, M is hydrogen or a cation, such as alkali metal (e.g., lithium, sodium, potassium), alkaline earth metal (beryllium, magnesium, calcium, strontium, barium), or ammonium. This type of surfactant is sometimes classified as an imidazoline-type amphoteric surfactant, although it should be recognized that it does not necessarily have to be derived, directly or indirectly, through an imidazoline intermediate. Suitable materials of this type are marketed under the tradename MIRANOL and are understood to comprise a complex mixture of species, and can exist in protonated and non-protonated species depending upon pH with respect to species that can have a hydrogen at $R^2$. All such variations and species are meant to be encompassed by the above formula.

Examples of surfactants of the above formula are mono-carboxylates and di-carboxylates. Examples of these materials include cocoamphocarboxypropionate, cocoamphocarboxypropionic acid, cocoamphocarboxyglycinate (alternately referred to as cocoamphodiacetate), and cocoamphoacetate.

Commercial amphoteric surfactants include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Betaine surfactants, i.e. zwitterionic surfactants, suitable for use in the conditioning compositions are those represented by the formula:

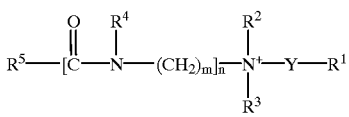

wherein: $R^1$ is a member selected from the group consisting of

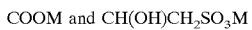

$R^2$ is lower alkyl or hydroxyalkyl; $R^3$ is lower alkyl or hydroxyalkyl; $R^4$ is a member selected from the group consisting of hydrogen and lower alkyl; $R^5$ is higher alkyl or alkenyl; Y is lower alkyl, preferably methyl; m is an integer from 2 to 7, preferably from 2 to 3; n is the integer 1 or 0; M is hydrogen or a cation, as previously described, such as an alkali metal, alkaline earth metal, or ammonium. The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like. It should be understood that the term "higher alkyl or alkenyl" includes mixtures of radicals which may contain one or more intermediate linkages such as ether or polyether linkages or non-functional substitutents such as hydroxyl or halogen radicals wherein the radical remains of hydrophobic character.

Examples of surfactant betaines of the above formula wherein n is zero which are useful herein include the alkylbetaines such as cocodimethylcarboxymethylbetaine, lauryldimethylcarboxymethylbetaine, lauryidimethyl-alpha-carboxyethylbetaine, cetyldimethylcarboxymethylbetaine, lauryl-bis-(2-hydroxyethyl)carboxymethylbetaine, stearyl-bis-(2-hydroxypropyl)carboxymethylbetaine, oleyldimethyl-gamma-carboxypropylbetaine, lauryl-bis-(2-hydroxypropyl)alpha-carboxyethylbetaine, etc. The sulfobetaines may be represented by cocodimethylsulfopropylbetaine, stearyldimethylsulfopropylbetaine, lauryl-bis-(2-hydroxyethyl)-sulfopropylbetaine, and the like.

Specific examples of amido betaines and amidosulfobetaines useful in the conditioning compositions include the amidocarboxybetaines, such as cocamidodimethylcarboxymethylbetaine, laurylamidodimethylcarboxymethylbetaine, cetylamidodimethylcarboxymethylbetaine, laurylamido-bis-(2-hydroxyethyl)carboxymethylbetaine, cocamido-bis-(2-hydroxyethyl)-carboxymethylbetaine, etc. The amidosulfobetaines may be represented by cocamidodimethylsulfopropylbetaine, stearylamidodimethylsulfopropylbetaine, laurylamido-bis-(2-hydroxyethyl)sulfopropylbetaine, and the like.

Nonionic Surfactants

The hair conditioning compositions of the present invention can comprise a nonionic surfactant. Nonionic surfactants include those compounds produced by condensation of alkylene oxide groups, hydrophilic in nature, with an organic hydrophobic compound, which may be aliphatic or alkyl aromatic in nature.

Preferred nonlimiting examples of nonionic surfactants for use herein include the following:

(1) polyethylene oxide condenses of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) condensation products of aliphatic alcohols having from about 8 to about 18 carbon atoms, in either straight chain or branched chain configurations, with ethylene oxide, e.g., a coconut alcohol ethylene oxide condense having from about to about moles of ethylene oxide per mole of coconut alcohol, the coconut alcohol fraction having from about 10 to about 14 carbon atoms;

(4) long chain tertiary amine oxides of the formula $[R^1R^2R^3N \rightarrow O]$ where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;

(5) long chain tertiary phosphine oxides of the formula $[RR'R''P \rightarrow O]$ where R contains an alkyl, alkenyl or monohydroxyalkyl radical ranging from about 8 to about 18 carbon atoms in chain length, from 0 to about 10 ethylene oxide moieties and from 0 to 1 glyceryl moieties and R' and R" are each alkyl or monohydroxyalkyl groups containing from about 1 to about 3 carbon atoms;

(6) long chain dialkyl sulfoxides containing one short chain alkyl or hydroxy alkyl radical of from 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to 1 glyceryl moieties;

(7) alkyl polysaccharide (APS) surfactants (e.g. alkyl polyglycosides), examples of which are described in U.S. Pat. No. 4,565,647, which is incorporated herein by reference in its entirety, and which discloses APS surfactants having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); a preferred material is alkyl polyglucoside which is commercially available from Henkel, ICI Americas, and Seppic; and (8) polyoxyethylene alkyl ethers such as those of the formula $RO(CH_2CH_2)_nH$ and polyethylene glycol (PEG) glyceryl fatty esters, such as those of the formula $R(O)OCH_2CH(OH)CH_2(OCH_2CH_2)_nOH$, wherein n is from 1 to about 200, preferably from about 20 to about 100, and R is an alkyl having from about 8 to about 22 carbon atoms.

Other Optional Components

A wide variety of other components can optionally be formulated into the present composition. These include: other conditioning agents such as hydrolysed collagen, hydrolysed keratin, proteins, plant extracts, and nutrients; hair-hold polymers; other surfactants such as anionic surfactants; additional thickening agents and suspending agents such as xanthan gum, guar gum, hydroxyethylcellulose, methylcellulose, starch and starch derivatives; viscosity modifiers such as methanolamides of long chain fatty acids such as cocomonoethanolamide; pearlescent aids such as ethylene glycol distearate; preservatives such as benzyl alcohol, methyl paraben, propyl paraben and imidazolidinyl urea; solvents such as polyvinyl alcohol, ethyl alcohol and volatile and non-volatile silicone fluids of low molecular weight; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; sequestering agents, such as disodium ethylenediamine tetra-acetate; and polymer plasticizing agents, such as glycerin, disobutyl adipate, butyl stearate, and propylene glycol; and ultraviolet and infrared screening and absorbing agents such as octyl salicylate, and propellants such as fluorohydrocarbons, dimethyl ether, carbon dioxide, nitrogen, and LPG gas. Such optional ingredients generally are used individually at levels from about 0.01% to about 10.0%, preferably from about 0.05% to about 5.0% by weight of the composition.

METHOD OF USE

The hair conditioning compositions of the present invention are used in conventional ways to provide the conditioning benefits such as moistness, softness, free flowing, decreased stickiness, and static control. Such method of use depends on the type of composition employed but generally involves application of an effective amount of the product to the hair, which may then be rinsed from the hair (as in the case of hair rinses) or allowed to remain on the hair (as in the case of gels, lotions, sprays, mousses, and creams). "Effective amount" means an amount sufficient enough to provide a conditioning benefit. In general, from about 1 g to about 50 g of the hair conditioning composition is applied to the hair andlor the scalp. If the compositions are not in uniform condition, for example, separated into two phases, the compositions need to be mixed before use. The composition is distributed throughout the hair, typically by rubbing or massaging the hair and scalp. Preferably, the composition is applied to wet or damp hair prior to drying of hair. After such compositions are applied to the hair, the hair is dried and styled in accordance with the preference of the user. In the alternative, the composition is applied to dry hair, and the hair is then combed or styled in accordance with the preference of the user.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

The hair conditioning ingredients herein are expressed by weight percentage of the total compositions, unless otherwise specified.

The components shown below can be prepared by any conventional method well known in the art. A suitable method and formulation are as follows:

Examples I–VI

For Example I through VI, the combination of stearyltrimethylammonium chloride and L-glutamic acid, or MATMAC are added into water under agitation at above 70° C. Then, stearyl alcohol and cetyl alcohol are added with agitation. After cooled down below 60° C., other ingredients except for denatured ethyl alcohol and perfume are added to the above and agitated. After the obtained mixture is cooled down under 50° C., denatured ethyl alcohol and perfumes are added. The obtained composition provides smoothness and soft feel to the hair.

| Example No. | I | II | III | IV | V | VI |
|---|---|---|---|---|---|---|
| Pentaerythritol tetraisostearate | 0.50 | — | 0.25 | — | 0.25 | — |
| Trimethylolpropane triisostearate | — | 0.5 | — | 0.25 | — | 0.5 |
| Methyl myristate | 0.5 | — | 0.4 | — | — | — |
| Oleyl alcohol | — | — | — | — | 0.4 | — |
| Mineral oil | — | — | — | — | 0.3 | — |
| Octyl dodecyl isostearate | — | 0.3 | — | 0.25 | — | 0.3 |
| Stearyl alcohol | 4.0 | 2.8 | 2.0 | 2.8 | 4.0 | — |
| Cetyl alcohol | 6.0 | 4.2 | 3.0 | 4.2 | 3.0 | 7.0 |
| Solid paraffin | — | 1.0 | — | 1.0 | — | — |
| Stearamidopropyldimethylamine | 2.0 | 2.0 | 3.0 | 2.0 | — | 2.0 |
| L-Glutamic acid | 0.64 | 0.64 | 1.0 | 0.64 | — | 0.64 |
| MATMAC*1 | — | — | — | — | 0.25 | — |
| Silicon mixture*2 | 5.0 | 1.0 | — | 1.0 | 2.0 | 4.0 |
| Preservative | 0.2 | 0.3 | 0.2 | 0.25 | 0.1 | 0.5 |
| Perfume | 0.2 | 0.25 | 0.1 | 0.2 | 0.4 | 0.2 |
| Denatured ethyl alcohol | — | — | — | — | 10.0 | — |
| Water | ----- up to 100% ----- | | | | | |

*1MATMAC; monoalkyl trimethyl ammonium chloride having $C_{20}$—$C_{22}$ alkyls
*2Silicone mixture; 85%/15% (wt. basis) mixture of D5 cyclomethicone and dimethicone gum (weight average molecular weight of about 400,000 to about 600,000).

For Examples VII through X, All ingredients are added into a denatured ethyl alcohol under agitation. The obtained composition is packed into packages equipped with a spraying device to make a conditioning spray. The obtained composition provides smoothness and soft feel to the hair.

| Example No. | VII | VIII | IX | X |
|---|---|---|---|---|
| Pentaerythritol isostearate | 1.50 | — | — | 0.5 |
| Trimethylolpropane triisostearate | — | 1.0 | 1.5 | — |
| Methyl myristate | 1.50 | 1.0 | — | — |
| Oleyl alcohol | — | — | — | 0.5 |
| Mineral oil | — | — | 1.5 | — |
| Cetyl alcohol | — | 1.0 | — | — |
| MATMAC*1 | — | 0.2 | — | 0.2 |
| Preservative | 0.1 | 0.1 | 0.1 | 0.1 |
| Perfume | 0.1 | 0.1 | 0.1 | 0.1 |
| Denatured ethyl alcohol | ----- up to 100% ----- | | | |

*1MATMAC; monoalkyl trimethyl ammonium chloride having $C_{20}$—$C_{22}$ alkyls

What is claimed is:

1. A hair conditioning composition comprising:
   (a) from about 0.1% to about 10%, by weight of the composition, of a water-insoluble high molecular weight oily compound having a molecular weight of at least about 800, specific gravity of at least about 0.9, a liquid form at 25° C., and the following formula (I):

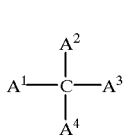

(I)

wherein $A^1$, $A^2$, $A^3$ and $A^4$ are independently an alkyl, alkenyl, aryl, alkylaryl, hydroxyalkyl, alkoxyl, alkoxyalkyl, acyl, acylalkyl, or alkylacyloxyl group having $C_1$ to about $C_{30}$ or of the formula —$(CH_2)_n$—OCR wherein R is a $C_1$ to about $C_{30}$ branched or straight chain alkyl or alkenyl and n is an integer from 1 to about 30;
   (b) from about 4% to about 10%, by weight of the composition, of a solid (at 25° C.) water-insoluble aliphatic compound; and
   (c) a carrier.

2. The hair conditioning composition according to claim 1 wherein at least two of $A^1$, $A^2$, $A^3$ and $A^4$ are independently the formula —$(CH_2)_n$—O—OCR wherein R is from $C_1$ to about $C_{30}$ of branched or straight chain alkyl or alkenyl and n is an integer from 1 to about 30, and the remainder of $A^1$, $A^2$, $A^3$ and $A^4$ are independently alkyl group having $C_1$ to about $C_{30}$.

3. The hair conditioning composition of claim 2 wherein the water-insoluble high molecular weight oily compound is selected from the group consisting of esters of a fatty acid of from $C_{12}$ to about $C_{22}$ with pentaerythritol, esters of a fatty acid of from $C_{12}$ to about $C_{22}$ with trimethylolalkane, and mixtures thereof.

4. The hair conditioning composition of claim 3 wherein the water-insoluble high molecular weight oily compound is selected from pentaerythritol tetraisostearate, trimethylolpropane triisostearate, pentaerythritol tetraoleate, trimethylolpropane trioleate, and mixtures thereof.

5. The hair composition according to claim 1, further comprising an additional conditioning agent selected from the group consisting of a nonvolatile water-insoluble low molecular weight oily compound, a cationic surfactant, a cationic polymer, a silicone compound, and mixtures thereof.

6. The hair conditioning composition according to claim 5 wherein the nonvolatile water-insoluble low molecular weight oily compound is selected from the group consisting of octyl dodecyl isostearate, methyl isostearate, oleyl alcohol, hydrocarbons having from about 10 to about 40 carbon atoms, and mixtures thereof.

7. The hair conditioning composition according to claim 1 wherein the solid water-insoluble aliphatic compound is selected from the group consisting of hydrocarbons having at least 20 carbon atoms, saturated fatty alcohols, fatty acids, fatty acid derivatives, fatty alcohol derivatives, steroids, and mixtures thereof.

8. The hair conditioning composition according to claim 7 wherein the solid water-insoluble aliphatic compound is selected from the group consisting of saturated fatty alcohols having from $C_{14}$ to about $C_{22}$.

9. The hair conditioning composition according to claim 1, wherein the composition comprises from about 0.1% to about 5%, by weight of the composition of the water-insoluble high molecular weight oily compound.

10. The hair conditioning composition according to claim 1, wherein the composition comprises from about 0.1% to about 1.5%, by weight of the composition, of the water-insoluble high molecular weight oily compound.

11. The hair conditioning composition according to claim 1, wherein the composition comprises from about 0.2% to about 5%, by weight of the composition, of the water-insoluble high molecular weight oily compound.

12. The hair conditioning composition according to claim 1, wherein the carrier is selected from the group consisting of water, lower alkyl alcohols, polyhydric alcohols, and mixtures thereof.

13. The hair conditioning composition according to claim 5, wherein the composition comprises from about 0.1% to about 10%, by weight of the composition, of the nonvolatile water-insoluble low molecular weight oily compound.

14. The hair conditioning composition according to claim 5, wherein the composition comprises from about 0.2% to about 5%, by weight of the composition, of the nonvolatile water-insoluble low molecular weight oily compound.

15. The hair conditioning composition according to claim 5, wherein the composition comprises from about 0.2% to about 2%, by weight of the composition, of the nonvolatile water-insoluble low molecular weight oily compound.

16. A method for conditioning hair, which method comprises applying an effective amount of the composition of claim 1 to the hair.

17. A hair conditioning composition comprising:
(a) from about 0.1% to about 5%, by weight of the composition, of a water-insoluble high molecular weight oily compound having a molecular weight of at least about 800, specific gravity of at least about 0.9, a liquid form at 25° C., and the following formula (I):

wherein $A^1$, $A^2$, $A^3$ and $A^4$ are independently an alkyl, alkenyl, aryl, alkylaryl, hydroxyalkyl, alkoxyl, alkoxyalkyl, acyl, acylalkyl, or alkylacyloxyl group having $C_1$ to about $C_{30}$ or of the formula —$(CH_2)_n$—OCR wherein R is a $C_1$ to about $C_{30}$ branched or straight chain alkyl or alkenyl and n is an integer from 1 to about 30;
(b) from about 4% to about 10%, by weight of the composition, of a solid (at 25° C.) water-insoluble aliphatic compound comprising saturated fatty alcohol having from $C_{14}$ to about $C_{22}$; and
(c) a carrier.

18. The hair conditioning composition according to claim 17, wherein the water-insoluble high molecular weight oily compound is selected from the group consisting of pentaerythritol tetraisostearate, trimethylolpropane triisostearate, pentaerythritol tetraoleate, trimethylolpropane trioleate, and mixtures thereof.

* * * * *